United States Patent [19]
Von Unge

[11] Patent Number: 5,929,244
[45] Date of Patent: Jul. 27, 1999

[54] PROCESS FOR THE OPTICAL PURIFICATION OF ENANTIOMERICALLY ENRICHED BENZIMIDAZOLE DERIVATIVES

[75] Inventor: Sverker Von Unge, Fjärås, Sweden

[73] Assignee: Astra Aktiebolag, Sodertalje, Sweden

[21] Appl. No.: 08/676,215

[22] PCT Filed: Jun. 26, 1996

[86] PCT No.: PCT/SE96/00841

§ 371 Date: Jul. 19, 1996

§ 102(e) Date: Jul. 19, 1996

[87] PCT Pub. No.: WO97/02261

PCT Pub. Date: Jan. 23, 1997

[30] Foreign Application Priority Data

Jul. 3, 1995 [SE] Sweden .................. PCT/SE95/00817

[51] Int. Cl.$^6$ .................................................. C07D 401/12
[52] U.S. Cl. .................... 546/273.7; 546/183; 548/307.1
[58] Field of Search ................. 546/273.7, 183; 548/307.1

[56] References Cited

FOREIGN PATENT DOCUMENTS

| | | |
|---|---|---|
| 0005129 | 10/1979 | European Pat. Off. . |
| 0268956 | 11/1987 | European Pat. Off. . |
| 0174726 | 4/1989 | European Pat. Off. . |
| 0434999 | 7/1991 | European Pat. Off. . |
| 4035455 | 5/1992 | Germany . |
| 2163747 | 3/1986 | United Kingdom . |
| 9427988 | 12/1994 | WIPO . |
| 9515962 | 6/1995 | WIPO . |
| 9702261 | 6/1996 | WIPO . |

OTHER PUBLICATIONS

Eur. J. Biochem, 166 (1987), pp. 453–459—Sigrist–Nelson, et al., Ro 18–5364, a potent new inhibitor of the gastric (H+ + K+)–ATPase.

Chem. Pharm. Bull., vol. 42, No. 3, (1994), pp. 718–720, Synthesis and Antiulcer Activities . . . , Yamada, et al.

*Primary Examiner*—Jane Fan
*Attorney, Agent, or Firm*—White & Case L.L.P.

[57] ABSTRACT

Process for the optical purification of the single enantiomers of some 2-sulphinyl-1H-benzimidazole derivatives and another structurally related sulphoxide from the respective enantiomerically enriched preparation thereof.

16 Claims, No Drawings

5,929,244

1

PROCESS FOR THE OPTICAL PURIFICATION OF ENANTIOMERICALLY ENRICHED BENZIMIDAZOLE DERIVATIVES

TECHNICAL FIELD

The present invention relates to a process for the optical purification of enantiomerically enriched preparations of some 2-(pyridinylmethylsulphinyl)-1H-benzimidazole derivatives as well as another structurally related sulphoxide.

PRIOR ART

There are a large number of patents and patent applications disclosing different substituted 2-(pyridinylmethylsulphinyl)-1H-benzimidazoles and structurally related sulphoxides. This dass of compounds has properties making the compounds useful as inhibitors of gastric acid secretion. For example the compound (5-methoxy-2-[[(4-methoxy-3,5-dimethyl-2-pyridinyl)-methyl]sulphinyl]-1H-benzimidazole), having the generic name omeprazole, and therapeutically acceptable salts thereof are described in EP 5129. Omeprazole and its alkaline salts are effective gastric acid secretion inhibitors, and are useful as antiulcer agents. Other compounds also effective as gastric add secretion inhibitors are the compounds 2-[[[3-methyl-4-(2,2,2-trifluoroethoxy)-2-pyridinyl]methyl]sulphinyl]-1H-benzimidazole having the generic name lansoprazole, described in EP-A1-174726; 2-[[[4-(3-methoxypropoxy)-3-methyl-2-pyridiny]methyl]sulphinyl]-1H-benzimidazole having the generic name pariprazole, described in EP 268956; 2-[[2-(N-isobutyl-N-methylamino) benzyl]sulphinyl]-1H-benzimidazole having the generic name leminoprazole, described in GB 2163747 and 2-[(4-methoxy-6,7,8,9-tetrahydro-5H-cyclohepta[b]pyridin-9-yl) sulphinyl]-1H-benzimidazole which is described in EP 434999.

These compounds omeprazole, lansoprazole, pariprazole and leminoprazole all have a stereogenic centre at the sulphur atom and thus exist as two stereoisomers (enantiomers). The compound 2-[(4-methoxy-6,7,8,9-tetrahydro-5H-cyclohepta[b]pyridin-9-yl)sulphinyl]-1H-benzirnidazole has two stereogenic centers, one centre at the methine carbon atom adjacent to the sulphur atom and one at the sulphur atom. Thus, this compound exists as four stereoisomers (two pair of enantiomers). Even though the 2-(pyridinylmethylsulphinyl)-1H-benzimidazole class of chiral sulphoxides, including omeprazole, have been described in the scientific literature since the late seventies, there is not yet any efficient asymmetric process reported for the synthesis of the single enantiomers thereof. The single enantiomers of pharmacologically active compounds have met an increased interest in the last years because of improved pharmacokinetic and biological properties. Therefore, there is a need for a process that can be used in large scale for the preparation of the single enantiomers of omeprazole and of other optical pure omeprazole analogues. Generally, asymmetric processes for obtaining chiral sulphoxides afford optically active sulphoxides in enantiomerically enriched forms rather than in pure single enantiomeric forms unless the processes are enzymatic transformations or resolution methods. Therefore, there is also a need for a method that can be used in large scale for the enhancement of optical purity for enantiomerically enriched preparations of optically active omeprazole and other optically active omeprazole analogues.

2

Prior art discloses processes for resolution of different substituted 2-(2-pyridinylmethylsulphinyl)-1H-benzimidazoles. For example in DE 4035455 and WO 94/27988 such resolution processes are described. These processes involve reaction steps wherein a diastereomeric mixture is synthesised from the racemate of the corresponding substituted 2-(2-pyridinylmethylsulphinyl)-1H-benzimidazoles. The diastereomers are then separated and finally the separated diastereomer is converted to the optically pure sulphoxide in a hydrolytic step. These resolution methods involving diastereomeric intermediates, suffer from at least three fundamental disadvantages namely:

1) The substituted 2-(2-pyridinylimethylsulphinyl)-1H-benzimidazole, as a racemic intermediate, has to be further processed in a couple of reaction steps before the single enantiomers can be obtained.

2) The resolution processes involve complicated separation steps.

3) There is a large waste of highly refined material when the unwanted stereoisomer, in the form of the opposite diastereomer, is discarded.

Further, prior art disdoses for instance enantioselective synthesis of a 2-(2-pyridinylmethylsulphinyl)-1H-benzimidazole derivative, namely the single enantiomers of the sulphoxide agent (5,7-dihydro-2-[[(4-methoxy-3-methyl-2-pyridinyl)methyl]-sulphinyl]-5,5,7,7-tetramethylindeno-[5,6-d]-imidazol-6-(1H)-one) see Euro. J. Biochem. 166 (1987) 453–459. This process is based on an enantioselective oxidation of the corresponding prochiral sulphide to said sulphoxide. The authors state that the crude product of the sulphoxide, showing an enantiomeric excess (e.e.) of about 30%, can be purified to optical pure sulphoxide [(e.e.)>95%] by several steps of crystallisation. However, the yields and the number of crystallisation steps are not reported. This proposed crystallization method is not suitable for the kind of substances according to the compounds of formula Ia–Ie in the present application.

SUMMARY OF THE INVENTION

The object of the present invention is to provide a novel process for the enhancement of the optical purity (enantiomeric excess, e.e.) for enantiomerically enriched preparations of omeprazole, lansoprazole, pariprazole, leminoprazole and 2-[(4-methoxy-6,7,8,9-tetrahydro-5H-cyclohepta[b]pyridin-9-yl)sulphinyl[-1H-benzimidazole. Surprisingly, the racemates of these compounds are very selectively precipitated from a solvent yielding the single enantiomers with an enhanced optical purity.

The process of the invention is defined in claim 1 and further preferred embodiments of the invention are disclosed in claims 2–9. Preferred compounds prepared by the new process are defined in claims 10–19.

DETAILED DESCRIPTION OF THE INVENTION

The process of the present invention is characterised by the steps of treating an enantiomerically enriched preparation of optically active omeprazole of the formula Ia

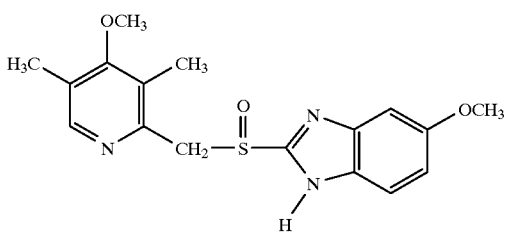

or of optically active lansoprazole of the formula Ib

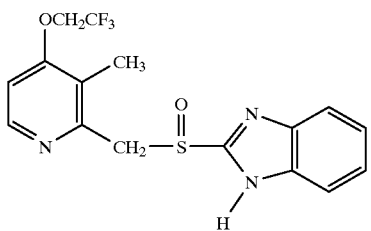

or of optically active pariprazole of the formula Ic

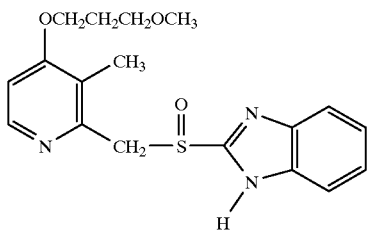

or of optically active lerninoprazole of the formula Id

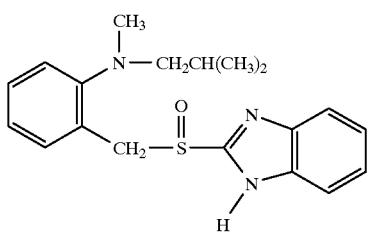

or of optically active 2-[(4-methoxy-6,7,8,9-tetrahydro-5H-cydohepta[b]pyridin-9-yl)sulphinyl]-1H-benzimnidazole of the formula Ie

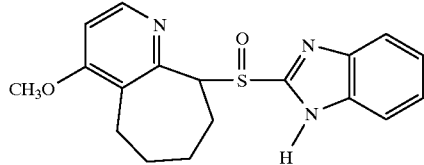

with a solvent from which the racemate is selectively precipitated. The precipitated benzimidazole derivative as a racemate, or as a racemate together with a small amount of the desired enantiomer is filtered off and the single enantiomer of the benzimidazole derivative, either as its (−)-enantiomer or as its (+)-enantiomer, with a dramatically enhanced optical purity is obtained by removing the solvent of the filtrate. The solvent is preferably removed by evaporation. The substituted 2-(2-pyridinylmethylsulphinyl)-1H-benzimidazole, to be treated in the process, is preferably omeprazole.

The precipitation is carried out in a protic or a non-protic solvent. The solvent facilitate the crystallisation and is necessary for the separation. The choice of solvent from which the racemate is precipitated is not essential for the process. Preferably the solvent is an organic solvent. A suitable organic solvent can be a ketone such as acetone or 2-butanone, or an ester such as ethyl acetate, or an alcohol such as ethanol, or a nitrile such as acetonitrile, or a hydrocarbon such as toluene. The solvent may also be an ether, an amide or any other organic solvent from which the racemate of the compounds according to formula Ia–Ie can be selectively precipitated. The solvent may also be a mixture of different organic solvents or a mixture of water and organic solvents. Preferably the solvent is one selected among acetone, toluen or acetonitril.

The temperature is not important for the process of the invention. However, if the temperature is too high the solubility increases, the selectivity decreases and the compound decomposes. Therefore, room temperature is preferred, but also temperatures below room temperature are suitable.

Thus, a preferred feature of the process of the invention is that the racemates of the compounds according to formula Ia–Ie surprisingly are very selectively crystallised from an organic solvent. A dramatically enhancement of the enantiomeric excess of the (−)-enantiomer or the (+)-enantiomer of the present compounds is obtained in the mother liquor (filtrate), even after only one racemate crystallisation. Therefore, the process becomes highly effective. Consequently, the single enantiomers can be obtained with a very high enantiomeric excess even from optically impure preparations. This means that a high enantioselectivity is not essential for the asymmetric synthesis of the said optical active compounds, e.g. the asymmetric oxidation of corresponding prochiral sulphide. Thus, a broader scope of synthetic methods can be considered when choosing the most appropriate asymmetric synthesis processes for obtaining the compounds according to formula Ia–Ie. For example chemical yield, cost of reagents, reaction time and grade of dangerousness of handling reagents may thus be as important factors as enantioselectivety when making the choice of synthetic method.

The invention is illustrated more in detail by the following examples 1–16. The invention is illustrated together with an asymmetric synthesis in examples 7–9.

EXAMPLES

The enantiomeric excess value in each example given below gives an indication of the relative amount of each enantiomer. The value is defined as the difference between the relative percentages for the two enantiomers. Thus, for example, when the percentage of the (−)-enantiomer of the sulphoxide is 97.5% and the percentage for the (+)-enantiomer is 2.5%, the enantiomeric excess for the (−)-enantiomer is 95%.

The enantiomeric composition of each sulphoxide was determined by chiral HPLC on either a Chiralpak AD Column or a Chiral AGP Column under the following conditions:

Compound of formula Ia.

| | |
|---|---|
| Column | Chiralpak AD 50 × 4.6 mm |
| Eluent | iso-Hexane (100 ml), ethanol (100 ml) and acetic acid (10 μl) |
| Flow | 0.5 ml/min |
| Inj.vol. | 50 μl |
| Wavelength | 302 nm |
| Retention time for the (−)-enantiomer | 4.0 min |
| Retention time for the (+)-enantiomer | 5.8 min |

Compound of formula Ib.

| | |
|---|---|
| Column | Chiral AGP 100 × 4.0 mm |
| Eluent | Sodium phosfate buffer solution (pH 7.0), I = 0.025 (500 ml) and acetonitrile (70 ml) |
| Flow | 0.5 ml/min |
| Inj.vol. | 20 μl |
| Wavelength | 210 nm |
| Retention time for the (+)-enantiomer | 6.2 min |
| Retention time for the (−)-enantiomer | 7.2 min |

Compound of formula Ic.

| | |
|---|---|
| Column | Chiral AGP 100 × 4.0 mm |
| Eluent | Sodium phosfate buffer solution (pH 7.0), I = 0.025 (430 ml) and acetonitrile (70 ml) |
| Flow | 0.5 ml/min |
| Inj.vol. | 20 μl |
| Wavelength | 210 nm |
| Retention time for the (+)-enantiomer | 4.1 min |
| Retention time for the (−)-enantiomer | 6.8 min |

Compound of formula Id.

| | |
|---|---|
| Column | Chiralpak AD 50 × 4.6 mm |
| Eluent | iso-Hexane (200 ml) and ethanol (10 ml) |
| Flow | 0.5 ml/min |
| Inj.vol. | 50 μl |
| Wavelength | 285 nm |
| Retention time for the (−)-enantiomer | 9.0 min |
| Retention time for the (+)-enantiomer | 9.8 min |

Compound of formula Ie.

| | |
|---|---|
| Column | Chiralpak AD 50 × 4.6 mm |
| Eluent | iso-Hexane (150 ml) and 2-propanol (50 ml) |
| Flow | 0.4 ml/min |
| Inj.vol. | 50 μl |
| Wavelength | 285 nm |
| Retention time for the (−)-enantiomer of diasteremor A | 6.9 min |
| Retention time for the (+)-enantiomer of diasteremor A | 8.1 min |
| Retention time for the (+)-enantiomer of diasteremor B | 8.8 min |
| Retention time for the (−)-enantiomer of diasteremor B | 11.0 min |

The first diastereomer of compound (Ie) eluted on straight phase (achiral silica gel, see below) is named diastereomer A and second as diastereomer B.

Example 1

Enhancement of optical purity from 60% e.e. to 98.4% e.e. for (−)-5-methoxy-2-[[(4-methoxy-3,5dimethyl-2-pyridinyl)-methyl]sulphinyl]-1H-benzimidazole, (−)-(Ia)

2.35 g of a mixture of the enantiomers of 5-methoxy-2-[[(4-methoxy-3,5 dimethyl-2-pyridinyl)methyl]sulphinyl]-1H-benzimidazole (60% e.e., in favour of the (−)-enantiomer) as a yellow syrup was dissolved in 20 ml of acetonitrile. Almost immediately the racemate as a solid appeared and after 30 minutes in a refrigerator this white solid was filtered off. The solvent of the filtrate was evaporated to yield 1.2 g of the (−)-enantiomer of omeprazole as a yellow syrup with an optical purity of 98.4% e.e.

Example 2

Enhancement of optical purity from 20% e.e to 91.4% e.e for (−)-5-methoxy-2-[[(4-methoxy-3,5-dimethyl-2-pyridinyl)-methysulphinyl]-1H-benzimidazole. (−)-(Ia)

2.35 g of a mixture of the enantiomers of 5-methoxy-2-[[(4-methoxy-3,5 dimethyl-2-pyridinyl)methyl]sulphinyl]-1H-benzirnidazole (20% e.e., in favour of the (−)-enantiomer as a yellow syrup was dissolved in 20 ml of 2-butanone. Almost immediately the racemate as a solid appeared and after one hour in a refrigerator this white solid was filtered off. The solvent of the filtrate was evaporated to yield 0.48 g of the (−)-enantiomer of omeprazole as a yellow syrup with an optical purity of 91.4% e.e.

Example 3

Enhancement of optical purity from 50% e.e. to 97.3% e.e. for (−)-5-methoxy-2-[[(4-methoxy-3,5dimethy-2-pyridinyl)-methyl]sulphinyl]-1H-benzimidazole, (−)-(Ia)

2.35 g of a mixture of the enantiomers of 5-methoxy-2-[[(4-methoxy-3,5 -dimethyl-2-pyridinyl)methyl]sulphinyl]-1H-benzimidazole (50% e.e., in favour of the (−)-enantiomer) as a yellow syrup was dissolved in 20 ml of acetone. Almost immediately the racemate as a solid appeared and after one hour in a refrigerator this white solid was filtered off. The solvent of the filtrate was evaporated to yield 1.0 g of the (−)-enantiomer of omeprazole as a yellow syrup with an optical purity of 97.3% e.e.

Example 4

Enhancement of optical purity from 80% e.e. to 95.4% e.e. for (+)-5-methoxy-2-[[(4-methoxy-3,5-dimethy-2-pyridinyl)-methyl]sulphinyl]-1H-benzimidazole, (+)-(Ia)

2.35 g of a mixture of the enantiomers of 5-methoxy-2-[[(4-methoxy-3,5-dimethyl-2-pyridinyl)methyl]sulphinyl]-1H-benzimidazole (80% e.e., in favour of the (+)-enantiomer) as a yellow syrup was dissolved in 20 ml of ethyl acetate. Almost immediately the racemate as a solid appeared and after one hour in a refrigerator this white solid was filtered off. The solvent of the filtrate was evaporated to yield 1.7 g of the (+)-enantiomer of omeprazole as a yellow syrup with an optical purity of 95.4% e.e.

Example 5

Enhancement of optical purity from 40% e.e. to 88.7% e.e. for (+)-5-methoxy-2[[(4-methoxy-3,5-dimethyl-2-pyridinyl)methyl]sulphinyl]-1H-benzimidazole, (+)-(Ia)

2.35 g of a mixture of the enantiomers of 5-methoxy-2-[[(4-methoxy-3,5dimethyl-2-pyridinyl)methyl]sulphinyl]-1H-benzimidazole (40% e.e., in favour of the (+)-enantiomer) as a yellow syrup was dissolved in 20 ml of ethanol. Almost immediately the racemate as a solid appeared and after one hour in a refrigerator this white solid was filtered off. The solvent of the filtrate was evaporated to yield 1.0 g of the (+)-enantiomer of omeprazole as a yellow syrup with an optical purity of 88.7% e.e.

Example 6

Enhancement of optical purity from 30% e.e. to 97.0% e.e. for (+)-5-methoxy-2-[[(4-methoxy-3,5-dimethyl-2-pyridinyl)-methyl]sulphinyl]-1H-benzimidazole, (+)-(Ia)

2.35 g of a mixture of the enantiomers of 5-methoxy-2-[[(4-methoxy-3,5-dimethyl-2-pyridinyl)methyl]sulphinyl]-1H-benzimidazole (30% e.e., in favour of the (+)-enantiomer) as a yellow syrup was dissolved in 20 ml of toluene. Almost immediately the racemate as a solid appeared and after one hour in a refrigerator this white solid was filtered off. The solvent of the filtrate was evaporated to yield 0.62 g of the (+)-enantiomer of omeprazole as a yellow syrup with an optical purity of 97.0% e.e.

Example 7

Asymmetric synthesis followed by optical purification of (+)-5-methoxy-2-[[(4-methoxy-3,5-dimethyl-2-pyridinyl)methyl]sulphinyl]-1H-benzimidazole, (+)-(Ia)

A mixture of 5-methoxy-2-[[(4-methoxy-3,5-dimethyl-2-pyridinyl)-methyl]thio]-1H-benzimidazole (0.47 g, 1.46 mmol), (3'S,2R)-(−)-N-(phenylsulphonyl)-(3,3-dichlorocamphoryl)oxaziridine (0.55 g, 1.46 mmol), triethylamine (0.07 ml, 0.5 mmol) and carbon tetrachloride 20 ml was stirred for 96 hours at ambient temperature. After removal of the solvent the residue was dissolved in methylene chloride (25 ml). The mixture was extracted with two portions of aqueous solutions of sodium hydroxide (0.1 M, 15 ml). The combined aqueous solutions were neutralised with an aqueous solution of ammonium chloride in the presence of methylene chloride. The phases were separated and the aqueous solution was extracted with two portions of methylene chloride. The combined organic solutions were dried over sodium sulphate and then the solvent was removed. The residue (200 mg, 40% e.e) was dissolved in 2-butanone (3 ml) and the formed solid was filtered off. The solvent of the filtrate was evaporated to yield 0.11 g (22%) of the title compound with an optical purity of 94% e.e.

Example 8

Asymmetric synthesis followed by optical purification of (−)-5-methoxy-2-[[(4-methoxy-3,5-dimethyl-2-pyridinyl)methyl]sulphinl]-1H-benzimidazole, (−)-(Ia)

1.6 kg (5.0 mol) of 5-methoxy-2-[[(4-methoxy-3,5-dimethyl-2-pyridinyl)-methyl]thio]-1H-benzimidazole was dissolved in 5.0 l of ethyl acetate. To the solution was added 31 ml (1.7 mol) of water. To the mixture was added 856 ml (5.0 mol) of (−)-diethyl D-tartrate, 744 ml (2.5 mol) of titanium(IV) isopropoxide and 435 ml (2.5 mol) of diisopropylethylamine at room temperature. The addition of 830 ml (4.5 mol) cumene hydroperoxide was then performed at 30° C. After stirring for one hour at 30° C. the reaction was complete. Chiral and achiral chromatographic analyses showed that the mixture consisted of 71.4% sulphoxide with an enantiomeric excess (e.e.) of 72.9%. The mixture was cooled to 10° C. and after addition of 1.7 l of isooctane, the product was extracted three times with an aqueous ammonia (12%) solution with a total volume of 10 l. The combined aqueous phases were neutralised by addition of 1.5 l of concentrated acetic acid in the presence of ethyl acetate (3 l). The phases were separated and the aqueous phase was extracted with ethyl acetate (3 l). The solvent of the combined organic solutions was removed and at the end of the evaporation acetonitrile (1.5 l) was added to facilitate the removal of solvent. Acetone (2.5 l) was added to precipitate the racemate of omeprazole which was filtered off (254 g). HPLC-analyses (achiral and chiral columns) of the filtrate showed that this solution consited of 88% sulphoxide with an optical purity of 96.3% e.e. and thus the optical purity has been improved from 72.9% e.e. to 96.3% e.e. simply by one precipitation of racemic omeprazole. Further, a content analysis (HPLC) of the filtrate showed that the yield was 0.8 kg (46%). The (−)-enantiomer of 5-methoxy-2-[[(4-methoxy-3,5-dimethyl-2-pyridinyl)methyl]sulphinyl]-1H-benzimidazole was not isolated in its neutral form but further processed to corresponding sodium salt.

Example 9

Asymmetric synthesis followed by optical purification of (+)-5-methoxy-2-[[(4-methoxy-3,5-dimethyl-2-pyridinyl)methyl]sulphinyl]-1H-benzimidazole, (+)-(Ia)

1.6 kg (5.0 mol) of 5-methoxy-2-[[(4-methoxy-3,5-dimethyl-2-pyridinyl)-methyl]thio]-1H-benzimidazole was dissolved in 7.5 l of ethyl acetate. To the solution was added 31 ml (1.7 mol) water. To the mixture was added 856 ml (5.0 mol) of (+)-diethyl L-tartrate, 744 ml (2.5 mol) of titanium (IV) isopropoxide and 436 ml (2.5 mol) diisopropylethylamine at room temperature. The addition of 830 ml (4.5 mol) cumene hydroperoxide was then performed at 30° C. After stirring for one hour at 30° C. the reaction was complete. Chiral and achiral chromatographic analyses showed that the mixture consited of 75% sulphoxide with an enantiomeric excess (e.e.) of 80%. The mixture was cooled to 10° C. and after addition of 1.5 l of isooctane and ethyl acetate (0.5 l), the product was extracted three times with an aqueous ammonia (12%) solution with a total volume of 14 l. The combined aqueous phases were neutralised by addition of 1.5 l of concentrated acetic acid in the presence of ethyl acetate (4 l). The phases were separated and the aqueous phase was extracted with ethyl acetate (4 l). The solvent of the combined organic solutions was removed. Acetone (3.0 l) was added to precipitate the racemate of omeprazole which was filtered off. HPLC—analyses (achiral and chiral columns) of the filtrate showed that this solution consisted of 90% sulphoxide with an optical purity of 95% e.e. and thus the optical purity has been improved from 80% e.e. to 95% e.e. simply by one precipitation of racemic omeprazole. Further, a content analysis (HPLC) of the filtrate showed that the yield was 1.0 kg (58%). The (+)-enantiomer of 5-methoxy-2-[[(4-methoxy-3,5-dimethyl-2-pyridinyl)methyl]sulphinyl]-1H-benzimidazole was not isolated in its neutral form but further processed to corresponding sodium salt.

The starting material in form of enantiomerically enriched preparations for the optical purification of one of the compounds according to formulas Ib, Ic, Id or Ie is prepared as described in examples 8 and 9.

Example 10

Enhancement of the optical purity of two of the stereoisomers of 2-[(4-methoxy-6,7,8,9-tetrahydro-5H-cyclohepta[b]pyridin-9-yl)sulphinyl]-1H-benzimidazole, (Ie).

In the following example, the first diastereomer of the title compound eluted on straight phase (silica gel) is named diastereomer A and second as diastereomer B. The stereoisomeric composition of the title compound in a crude mixture as a syrup (0.25 g) was as follows; The ratio of diastereomers was 4:3 in favour of diastereomer A. The optical purity of the (−)-enantiomer of diastereomer A was 76% e.e. and the optical purity of the (+)-enantiomer of diastereomer B was 68% e.e.

Separation of the diastereomers. A chromatographic preparation (methanol-methylene chloride 0 to 5%) afforded a separation of the two diastereomers. Thus, the (−)-enantiomer of diastereomer A was obtained as a syrup (0.145 g) with an optical purity of 77% e.e. The (+)-enantiomer of diastereomer B was also obtained as a syrup (0.085 g) with an optical purity of 68% e.e., however, diastereomer B was contaminated with ca. 10% of diastereomer A.

Optical purification: The optical purity of the (−)-enantiomer of diastereomer A was enhanced by the addition of ca. 2 ml of acetonitrile to the enantiomerically enriched preparation of diastereomer A(0.145 g). After stirring over night, the formed precipitate (almost racemic diastereomer A) was filtered off and the solvent of the filtrate was removed by film evaporation. Thus, there was obtained 85 mg of the (−)-enantiomer of diastereomer A as a syrup with an optical purity of 88% e.e. The optical purity of the (+)-enantiomer of the diastereomer B was enhanced in a similar way. Thus, by addition of acetonitrile (2 ml) to the enantiomerically enriched preparation of diastereomer B (0.085 g) followed by stirring over night resulted in a precipitate which was filtered off. From the filtrate there was obtained 0.050 g of the (+)-enantiomer of diastereomer B with an optical purity of 95% e.e.

Example 11

Enhancement of the optical purity of (−)-2-[[[3-methyl-4-(2,2,2-trifluoroethoxy)-2-pyridinyl]methyl]sulphinyl]-1H-benzimidazole, (−)-(Ib).

1.2 g of a crude mixture of the title compound with an enantiomeric excess (e.e.) of 55% was treated with acetonitrile (a few ml) and there was obtained a precipitate that was removed by filtration. Evaporation of the filtrate afforded an oil with enhanced optical purity. Repeating this procedure a couple of times afforded 0.63 g of the desired compound as an oil with an optical purity of 99.5% e.e.

Example 12

Enhancement of the optical purity of (+)-2-[[[3-methyl-4-(2,2,2- trifluoroethoxy)-2-pyridinyl]methyl]sulphinyl]-1H-benzimidazole, (+)-(Ib).

0.85 g of a crude mixture of the title compound with an enantiomeric excess (e.e.) of 46% was treated with acetonitrile (a few ml) and there was obtained a precipitate that was removed by filtration. Evaporation of the filtrate afforded an oil with enhanced optical purity. Repeating this procedure a couple of times afforded 0.31 g of the desired compound as an oil with an optical purity of 99.6% e.e.

Example 13

Enhancement of the optical purity of (−)-2-[[[4-(3-methoxypropoxy)-3-methyl-2-pyridinyl]methyl]sulphinyl]-1H-benzimidazole, (−)-(Ic).

1.62 g of a crude mixture of the title compound with an enantiomeric excess (e.e.) of 90% was treated with acetonitrile (a few ml) and there was obtained a precipitate that could be removed by filtration. Concentrating the filtrate afforded 1.36 g of the title compound as an oil with an optical purity of 91.5% e.e.

Example 14

Enhancement of the optical purity of (+)-2-[[[4-(3-methoxypropoxy)-3-methyl-2-pyridinyl]methyl]sulphinyl]-1H-benzimidazole, (+)-(Ic).

1.63 of a crude mixture of the title compound with an enantiomeric excess (e.e.) of 91 % was treated with acetonitrile (a few ml) and there was obtained a precipitate that could be removed by filtration. Concentrating the filtrate afforded 1.1 g of the title compound as an oil with an optical purity of 96.0% e.e.

Example 15

Enhancement of the optical purity of (−)-2-[2-(N-isobutyl-N-methlamnino)benzylsulphinyl]benzimidazole, (−)-(Id).

1.6 g of a crude mixture of the title compound with an enantiomeric excess (e.e.) of 92% was treated with a small amount of acetonitrile in order to enhance the optical purity. A formed precipitate was removed by filtration. The solvent of the filtrate was removed by film evaporation and there was obtained 1.2 g of the desired compound as an oil. The optical purity of the material was 96% e.e. according to chiral HPLC.

Example 16

Enhancement of the optical purity of (+)-2-[2-(N-isobutyl-N-methylamino)benzylsulphinyl]benzimidazole (+)-(Id).

3.0 g of a crude mixture of the title compound (91% e.e.), contaminated with (−)-diethyl D-tartrate, was dissolved in 40 ml of a mixture of ethyl acetate and hexane (10% EtOAc). A formed precipitate (140 mg) was removed by filtration. The solvent of the filtrate was removed by film evaporation and the residue was purified by column chromatography (silica gel, EtOAc/Hexane 15:85). There was obtained 0.95 g of the title compound showing an optical purity of 96% e.e. according to chiral HPLC.

I claim:

1. A process for the optical purification of enantiomerically enriched preparations of one of the compounds according to formulas Ia, Ib, Ic, Id and Ie

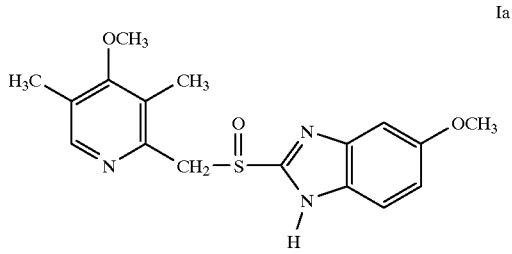

Ia

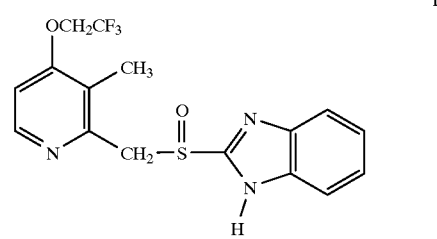

Ib

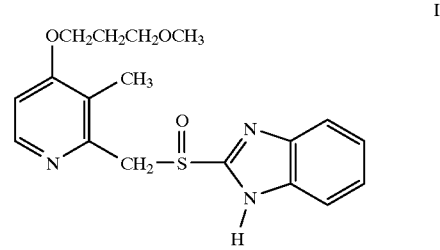

Ic

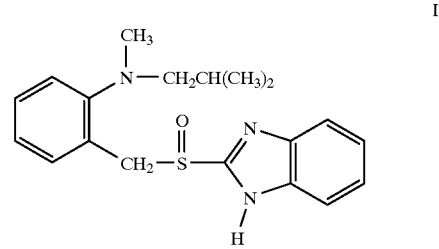

Id

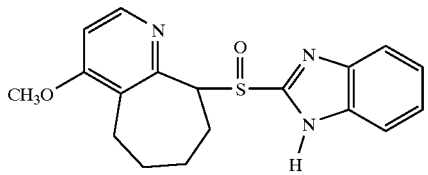

comprising the steps of treating an enantiomerically enriched preparations of the compound in favour of its (+) or (−)-enantiomer at room temperature or below with an organic solvent selected from the group consisting of ketones, esters, alcohol, nitriles, hydrocarbons, ethers, amides and mixtures thereof from which the racemate of the compound is selectively precipitated, filtering off the precipitated racemate and removing the solvent to yield the single enantiomer with an enhanced optical purity.

2. The process according to claim 1 wherein the optical purity of the (−)-enantiomer of the compound according to formula Ia is enhanced.

3. A process according to claim 1 wherein the optical purity of the (+)-enantiomer of the compound according to formula Ia is enhanced.

4. The process according to claim 1 wherein the solvent is removed by evaporation.

5. The process according to claim 1 wherein the enantiomerically enriched preparation is treated with a mixture of organic solvents.

6. The process according to claim 1 wherein water is mixed with the organic solvent and enantiomerically enriched preparation is treated with the mixture.

7. The process according to claim 6, wherein the mixture of water and one or more organic solvents contains <50% water.

8. The process according to claim 1, wherein the organic solvent is acetone, acetonitrile or toluene.

9. The process according to any of claims 1, 4 and 5–8, wherein the compound is (−)-2-[[[3-methyl4-(2,2,2-trifluoroethoxy)-2-pyridinyl]-methyl]sulphinyl]-1H-benzimidazole.

10. The process according to any of claims 1, 4 and 5–8, wherein the compound is (+)-2-[[[3-methyl-4-(2,2,2-trifluoroethoxy)-2-pyridinyl]-methyl]sulphinyl]-1H-benzimidazole.

11. The process according to claim 1, wherein the compound is (−)-2-[[[4-(3-methoxypropoxy)-3-methyl-2-pyridinyl]-methyl]sulphinyl]-1H-benzimidazole.

12. The process according to claim 1, wherein the compound is (+)-2-[[[4-(3-methoxypropoxy)-3-methyl-2-pyridinyl]-methyl]sulphinyl]-1H-benzimidazole.

13. The process according to claim 1, wherein the compound is (−)-2-[2-(N-isobutyl-N-methylamino) benzylsulphinyl]-benzimidazole.

14. The process according to claim 1, wherein the compound is (+)-2-[2-(N-isobutyl-N-methylamino) benzylsulphinyl]-benzimidazole.

15. The process according to claim 1, wherein the compound is (−)-2-[(4-methoxy-6,7,8,9-tetrahydro-5H-cyclohepta[b]pyridin-9-yl)sulphinyl]-1H-benzimidazole.

16. The process according to claim 1, wherein the compound is (+)-2-[(4-methoxy-6,7,8,9-tetrahydro-5H-cyclohepta[b]pyridin-9-yl)sulphinyl]-1H-benzimidazole.

* * * * *

UNITED STATES PATENT AND TRADEMARK OFFICE
CERTIFICATE OF CORRECTION

PATENT NO. : 5,929,244
DATED : July 27, 1999
INVENTOR(S) : Von Unge

It is certified that error appears in the above-identified patent and that said Letters Patent is hereby corrected as shown below:

Title page

-- Related U.S. Application Data
[63] Continuation-in-part of Ser. 491,939, July 3, 1995, abandoned. --

Col. 1, line 6, insert -- This is a continuation-in-part of application Ser. No. 08/491,939, filed July 3, 1995, now abandoned. --

In claim 1, col. 11, line 12, delete "preparations" and insert therefor -- preparation --.

In claim 6, col. 11, line 30, before the word "enantiomerically", insert -- the --.

Signed and Sealed this

Twenty-third Day of May, 2000

Attest:

Q. TODD DICKINSON

*Attesting Officer*   *Director of Patents and Trademarks*